United States Patent [19]

Cook et al.

[11] Patent Number: 5,637,684
[45] Date of Patent: Jun. 10, 1997

[54] PHOSPHORAMIDATE AND PHOSPHOROTHIOAMIDATE OLIGOMERIC COMPOUNDS

[75] Inventors: Phillip D. Cook, Carlsbad; Oscar Acevedo, San Diego; Normand Hebert, San Marcos, all of Calif.

[73] Assignee: ISIS Pharmaceuticals, Inc., Carlsbad, Calif.

[21] Appl. No.: 200,638

[22] Filed: Feb. 23, 1994

[51] Int. Cl.$^6$ .......................... C07H 21/00; C07H 21/02; C07H 21/04; C07D 239/00
[52] U.S. Cl. .................. 536/23.1; 536/24.3; 536/24.5; 536/25.3; 544/242; 544/264; 568/8; 568/11; 568/36
[58] Field of Search ................ 536/22.1, 23.1, 536/24.1, 24.3, 24.5, 25.3; 514/44

[56] References Cited

U.S. PATENT DOCUMENTS

| | | | |
|---|---|---|---|
| 4,547,569 | 10/1985 | Letsinger et al. | 536/25.32 |
| 4,958,013 | 9/1990 | Letsinger | 536/24.5 |
| 5,218,103 | 6/1993 | Caruthers et al. | 536/25.33 |
| 5,272,250 | 12/1993 | Spielvogel et al. | 530/300 |

FOREIGN PATENT DOCUMENTS 0 219 342 A2  4/1987  European Pat. Off. .

OTHER PUBLICATIONS

Zhou et al. "Synthesis and Antitumor Activity of Polyphosphates Containing both Nitrogen Mustard and ipophilic Groups" Gaodeng Xuexiao Huaxue Xuebao 10(9):935–8 (English abstract provided) 1989.

Agrawal et al., "Oligodeoxynucleoside Phosphoramidates and Phosphorothioates as Inhibitors of Human Immunodeficiency Virus" *Proc. Natl. Acad. Sci* 85: 7079–7083 (1988).

Chu et al., "Derivatization of Unprotected Polynucleotides" *Nucleic Acids Research* 11: 6513–6529 (1983).

Dagle et al., "Targeted Degradation of mRNA in Xenopus Oocytes and Embryos Directed by Modified Olignucleotides: Studies of An2 and Cyclic in Embryogenesis", *Nucleic Acids Research* 18: 4751–4757 (1990).

Ecker et al., "Rational Screening of Oligonucleotide Combinatorial Libraries for Drug Discovery" *Nucleic Acids Research* 21: 1853–1856 (1993).

Eritja et al., "O–Aryl Phosphoramidites: Synthesis, Reactivity and Evaluation of Their Use for Solid–Phase Synthesis of Oligonucleotides", *Tetrahedron* 45: 721–730 (1990).

Froehler et al., "Phosphoramidate analogues of DNA: Synthesis and Thermal Stability of Heteroduplexes", *Nucleic Acid Research* 16: 4831–4839 (1988).

Jäger et al., "Oligonucleotide N–Alkylphosphoramidates: Synthesis and Binding to Polynucleotides", *Biochemistry* 27: 7237–7246 (1988).

Letsinger et al., "Cholesteryl–Conjugated Oligonucleotides: Synthesis, Properties, and Activity as Inhibitors of Replication of Human Immunodeficiency Virus in Cell Culture", *Proc. Natl. Acad. Sci* 86: 6553–6556 (1989).

Ohtsuka et al., New phosphoramidates as protecting groups in ribooligonucleotides synthesis *Nucleic Acids Research* 3: 653–660 (1976).

Wyatt et al., "Combinatorially Selected Guanosine–Quartet Structure is a Potent Inhibitor of Human Immunodeficiency Virus Envelope–Mediated Cell Fusion" *Proc. Natl. Acad. Sci* 91: 1356–1360 (1994).

Houghten, et al., "Generation and use of synthetic peptide combinatorial libraries for basic research and drug discovery" *Nature* 354: 84–86 (1991).

*Primary Examiner*—George C. Elliott
*Assistant Examiner*—Thomas G. Larson
*Attorney, Agent, or Firm*—Woodcock Washburn Kurtz Mackiewicz & Norris

[57] ABSTRACT

Compounds are provided having the structure:

$$E_1-O-L_0-O\underset{Y_0-N}{\overset{O}{\underset{|}{\overset{\diagup}{P}}}}\underset{T_0}{\overset{\diagdown}{X_0}}O\left[L_m-O\underset{Y_m-N}{\overset{O}{\underset{|}{\overset{\diagup}{P}}}}\underset{T_m}{\overset{\diagdown}{X_m}}O\right]_m L_{m+1}-O-E_2$$

wherein the L groups are spanner or linker units, the Y and T group are functional groups for interacting with target molecules of interest, the X groups are oxygen or sulfur and the E groups are H, conjugate groups or intermediate groups used during the synthesis of the compounds are prepared using H phosphonate type chemistry wherein the functional groups are added during an oxidization step.

21 Claims, No Drawings

PHOSPHORAMIDATE AND PHOSPHOROTHIOAMIDATE OLIGOMERIC COMPOUNDS

FIELD OF THE INVENTION

This invention is directed to oligomeric compounds having phosphoramidate or phosphorothioamidate monomer units that are connected together via spanner units. Each phosphoramidate and phosphorothioamidate unit is substituted, via a phosphoramidate linkage, with a tethered or untethered functional group. The oligomers are synthesized having either a random or a predefined sequences of units. Randomization can be effected independently at the functional group or at the spanners. The functional group on each of the monomeric units provides for binding of the oligomeric structures to proteins, nucleic acid, lipids and other biological targets. In preferred embodiments, the compounds of the invention act as inhibitors of enzymes such as phospholipase $A_2$. As inhibitors of phospholipases $A_2$ they are useful for the treatment of inflammatory diseases including atopic dermatitis and inflammatory bowel disease.

BACKGROUND OF THE INVENTION

Traditional processes of drug discovery involve the screening of complex fermentation broths and plant extracts for a desired biological activity or the chemical synthesis of many new compounds for evaluation as potential drugs. The advantage of screening mixtures from biological sources is that a large number of compounds are screened simultaneously, in some cases leading to the discovery of novel and complex natural products with activity that could not have been predicted otherwise. The disadvantages are that many different samples must be screened and numerous purifications must be carried out to identify the active component, often present only in trace amounts. On the other hand, laboratory syntheses give unambiguous products, but the preparation of each new structure requires significant amounts of resources. Generally, the de novo design of active compounds based on the high resolution structures of enzymes has not been successful.

In order to maximize the advantages of each classical approach, new strategies for combinatorial unrandomization have been developed independently by several groups. Selection techniques have been used with libraries of peptides (see Geysen, H. M., Rodda, S. J., Mason, T. J., Tribbick, G. & Schoofs, P. G., J. Immun. Meth. 1987, 102, 259–274; Houghten, R. A., Pinilla, C., Blondelle, S. E., Appel, J. R., Dooley, C. T. & Cuervo, J. H., Nature, 1991, 354, 84–86; Owens, R. A., Gesellchen, P. D., Houchins, B. J. & DiMarchi, R. D., Biochem. Biophys. Res. Commun., 1981, 181, 402–408), nucleic acids (see Wyatt, J. R., et al., Proc. Natl. Acad. Sci. USA, (in press); Ecker, D. J., Vickers, T. A., Hanecak, R., Driver, V. & Anderson, K., Nucleic Acids Res., 1993, 21, 1853–1856) and nonpeptides (see Simon, R. J., et al., Proc. Natl. Acad. Sci. USA, 1992, 89, 9367–9371; Zuckermann, R. N., et al., J. Amer. Chem. Soc., 1992, 114, 10646–10647; Bartlett, Santi, Simon, PCT WO91/19735; and Ohlmeyer, M. H., et al., Proc. Natl. Acad. Sci. USA, 1993, 90, 10922–10926). The techniques involve iterative synthesis and screening of increasingly simplified subsets of oligomers. Monomers or sub-monomers that have been utilized include amino acids and nucleotides both of which are bi-functional. Utilizing these techniques, libraries have been assayed for activity in either cell-based assays, or for binding or inhibition of purified protein targets.

A technique, called SURF (Synthetic Unrandomization of Randomized Fragments), involves the synthesis of subsets of oligomers containing a known residue at one fixed position and equimolar mixtures of residues at all other positions. For a library of oligomers four residues long containing three monomers (A, B, C), three subsets would be synthesized (NNAN, NNBN, NNCN, where N represents equal incorporation of each of the three monomers). Each subset is then screened in a functional assay and the best subset is identified (e.g. NNAN). A second set of libraries is synthesized and screened, each containing the fixed residue from the previous round, and a second fixed residue (e.g. ANAN, BNAN, CNAN). Through successive rounds of screening and synthesis, a unique sequence with activity in the assay can be identified. The SURF technique is described in Ecker, D. J., Vickers, T. A., Hanecak, R., Driver, V. & Anderson, K., Nucleic Acids Res., 1993, 21, 1853–1856. The SURF method is further described in PCT patent application WO 93/04204, the entire disclosure of which is herein incorporated by reference.

Phosphoramidates were note for use as protecting groups for ribooligonucleotide synthesis by Ohtsuka, E., et. al., Nucleic Acids Research, 1976, 3, 653. Oligonucleotides having a phosphoramidate link amino group at their 5' end were disclosed by Chu, B. C. F., et. al., Nucleic Acids Research, 1983, 11, 6513. Oligodeoxynucleotides (DNA) containing internucleotide phosphoramidate linkages have been synthesized by several groups. However, in each such synthesis, the phosphoramidate linkage has only been utilized to connect adjacent nucleosides, i.e. an internucleotide linkage. One of these synthesis was reported by Froehler, B., et. al., Nucleic Acids Research, 1988, 16, 4831–4838. As reported by Froehler, et. al., the stability of duplexes ranging from dimers to fifteen mers was studied to determine the ability of the oligonucleotides to hybridize to complementary diester oligonucleotides. Thermal denaturation revealed enhanced stability for dimers and trimers but less stability for longer sequences. Other phosphoramidite containing oligonucleotides are disclosed by Eritja, R. et. al., Tetrahedron, 1990, 45, 721; and Jager, A., et. al., Biochemistry, 1988, 27, 7237.

In U.S. Pat. No. 5,272,250, issued Dec. 21, 1993, boronated phosphoramidate compounds are disclosed. The disclosed compounds include a boron moiety connected through a tether to the nitrogen of the phosphoramidate. The boronated compound is present as either a monomer or linked to a nucleoside.

Modified oligodeoxynucleotides complementary to the RNA of human immunodeficiency virus 1 (HIV-1) were synthesized by Agrawal, S., et.al., Proc. Natl. Acad. Sci, USA., 1988, 85, 7079–7083). Among the modifications disclosed in this publication are phosphoramidate oligonucleotides. Groups attached to these phosphoramidates include butylamine, piperazidine, and morpholine. The interactions of these compounds to their target, i.e. RNA, was through an antisense mechanism utilizing normal Watson/Crick hydrogen bonding. Similar phosphoramidate containing oligonucleotides are further disclosed by Dagel, et. al., Nucleic Acids Research, 1990, 18, 4751.

Phosphoramidates oligonucleotides are also disclosed in European Patent Application 86307926.5, filed Oct. 14, 1986. In this patent, a number of functional groups are used for substituting onto the phosphoramidate nitrogen. As with others of the above referenced disclosures, again in this patent the groups linking the phosphoramidates are nucleosides of oligonucleotides.

A family of oligonucleotides of different lengths containing a cholesterol group or phenanthridinium group tethered via a phosphoramidate bond to an internucleoside phosphorous atom were synthesized and tested for activity in an HIV-1 assay by Letsinger, R. L., et.al., *Proc. Natl. Acad. Sci. USA,.* 1989, 86, 6553–6556). Two corresponding United States patents, U.S. Pat. Nos. 4,547,569 and 4,958,013, describes essentially the same structures.

In U.S. Pat. No. 5,218,103, issued Jun. 8, 1993, phosphorothioamidate oligonucleotides are disclosed. The phosphorothioamidate oligonucleotides disclosed in this patent are substituted with a variety of moieties on the phosphorothioamidate nitrogen.

In each of the foregoing disclosures, it is not known to use phosphoramidate linkage between any groups other than the nucleoside residues of oligonucleotides.

OBJECTS OF THE INVENTION

It is an object of this invention to provide novel phosphoramidate oligomeric compounds.

It is a further object of this invention to provide novel phosphorothioamidate oligomeric compounds.

It is yet a further object of this invention to provide novel phosphoramidate and phosphorothioamidate oligomeric compounds having fixed sequenced functional groups thereon.

It is yet a further object of this invention to provide novel phosphoramidate and phosphorothioamidate oligomeric compounds having random sequenced functional groups thereon.

BRIEF SUMMARY OF THE INVENTION

The present invention provides compounds of the structure

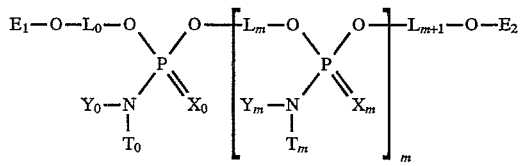

wherein $X_0$ and each $X_m$, independently, are O or S;

$Y_0$ and each $Y_m$, independently, are H, or $[Q_2]_j$—$Z_2$;

$T_0$ and each $T_m$, independently, are $[Q_1]_k$—$Z_1$, or together Y and T are joined in a nitrogen heterocycle;

$Q_1, Q_2, L_0, L_{m+1}$ and each $L_m$, independently, are $C_2$–$C_{10}$ alkyl, $C_2$–$C_{10}$ alkenyl, $C_2$–$C_{10}$ alkynyl, $C_4$–$C_7$ carbocylo alkyl or alkenyl, a heterocycle, an ether having 2 to 10 carbon atoms and 1 to 4 oxygen or sulfur atoms, a polyalkyl glycol, or $C_7$–$C_{14}$ aralkyl;

E1 and E2, independently, are H, a hydroxyl protecting group, an activated solid support, a conjugate group, a reporter group, a polyethylene glycol, alkyl, oligonucleotide, peptide nucleic acid, a phosphate, a phosphite, an activated phosphate, or an activated phosphite;

j and k independently are 0 or 1;

m is 1 to about 50;

$Z_1$ and $Z_2$, independently, are H, $C_1$–$C_2$ alkyl, $C_2$–$C_{20}$ alkenyl, $C_2$–$C_{20}$ alkynyl, $C_6$–$C_{14}$ aryl, $C_7$–$C_{15}$ aralkyl, a halogen, CH=O, $OR_1$, $SR_2$, $NR_3R_4$, C(=NH)$NR_3R_4$, CH($NR_3R_4$), NCH(=NH)$NR_3R_4$, CH($NH_2$)C(=O)OH, C(=O)$NR_3R_4$, C(=O)$OR_5$, a metal coordination group, a reporter group, a nitrogen-containing heterocycle, a purine, a pyrimidine, a phosphate group, a polyether group, or a polyethylene glycol group;

$R_1$ is H, alkyl having 1 to about 6 carbon atoms, or a hydroxyl protecting group;

$R_2$ is H, alkyl having 1 to about 6 carbon atoms, or a thiol protecting group;

$R_3$ and $R_4$ are, independently, H, alkyl having 1 to about 6 carbon atoms, or an amine protecting group; and $R_5$ is H, alkyl having 1 to about 6 carbon atoms, or an acid protecting group.

The invention further includes chimeric oligomeric compounds having a first region comprising a phosphodiester or phosphorothioate oligonucleotide and a second region comprising a region of Structure I above and where one of $E_1$ and $E_2$ groups of the Structure I region of the chimeric compound is the phosphodiester or phosphorothioate oligonucleotide and the other of the $E_1$ and $E_2$ groups is H. In further chimeric oligomeric compounds, the phosphodiester or phosphorothioate oligonucleotide region of the chimeric compound is positioned between two regions each of which is a region having the Structure I above.

DETAILED DESCRIPTION OF THE INVENTION

Compounds of the invention are shown by Structure I above. In Structure I, the bracketed portion of Structure I, herein referred to as a repeating unit or monomeric unit, includes either a phosphoramidate or phosphorothioamidate moiety that, in turn, bears a number of functional groups or fragments thereon. Certain of these groups, the groups "L", are used to link adjacent monomeric units together. For ease of understanding the invention these "L" groups are referred to as "spanner" groups. The spanner groups "link" the phosphoramidate or phosphorothioamidate moieties in an oligomeric backbone. These linking groups are also used to attach other groups to form chimeric structures. The spanner groups are, in essences, bi-valent in nature. In preferred compounds of the invention, the "spanner" groups are selected as dihydroxyl groups, i.e. groups having primary or secondary hydroxyl groups thereon.

The phosphoramidate or phosphorothioamidate moieties, besides being linked together by the spanner groups, serve also as the place for connecting certain other groups that impart "functional" properties to the oligomeric compounds of the invention. By varying these functional groups—diversity is incorporated into the compounds of the invention. The phosphoramidate or phosphorothioamidate moieties can be considered as being at least tri valent in nature—that is they are connected to at least two spanner groups (one on either side) and to one functional group. In actuality, they are penta valent when the X groups (the O or S) are considered.

The functional groups are attached to the phosphoramidate or phosphorothioamidate moieties with or without intervening tethers. In preferred embodiments of the invention they are connected to phosphoramidate or phosphorothioamidate moieties utilizing H phosphonate or H phosphorothioamidate intermediates. The function groups are connected to these intermediates by an oxidation mechanism—that is oxidizing the H phosphonate or H phosphorothioamidate intermediates to the final phosphoramidate and phosphorothioamidate states.

For the purposes of this specification, in the context of the invention and in reference to the above Structure I, alkyl, alkenyl, and alkynyl groups include but are not limited to substituted and unsubstituted straight chain, branch chain, and alicyclic hydrocarbons, including methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl and other higher carbon alkyl groups. Further examples include 2-methylpropyl, 2-methyl-4-ethylbutyl, 2,4-diethylpropyl, 3-propylbutyl, 2,8-dibutyldecyl, 6,6-dimethyl octyl, 6-propy-6-butyloctyl, 2-methylbutyl, 2-methylpentyl, 3-methylpentyl, 2-ethylhexyl and other branched chain groups, allyl, crotyl, propargyl, 2-pentenyl and other unsaturated groups, cyclohexane, cyclopentane, adamantane as well as other alicyclic groups, 3-penten-2-one, 3-methyl-2-butanol, 2-cyanooctyl, 3-methoxy-4-heptanal, 3-nitrobutyl, 4-isopropoxydodecyl, 4-azido-2-nitrodecyl, 5-mercaptononyl, 4-amino-1-pentenyl as well as other substituted groups.

Further, in the context of this invention, a straight chain compound means an open chain compound, such as an aliphatic compound, including alkyl, alkenyl, or alkynyl compounds; lower alkyl, alkenyl, or alkynyl as used herein include but are not limited to hydrocarbyl compounds from about 1 to about 6 carbon atoms. A branched compound, as used herein, comprises a straight chain compound, such as an alkyl, alkenyl, alkynyl, which has further straight or branched chains attached to the carbon atoms of the straight chain. A cyclic compound, as used herein, refers to closed chain compounds—that is, a ring of carbon atoms, such as a cyclic aliphatic or aromatic compound. The straight, branched, or cyclic compounds may be internally interrupted (i.e., alkylalkoxy or heterocyclic compounds). In the context of this invention, internally interrupted means that the carbon chains may be interrupted with heteroatoms such as O, N, or S; however, if desired, the carbon chain may have no heteroatoms.

Such compounds as noted above may be substituted or unsubstituted. In the context of this invention, substituted or unsubstituted, means that the compounds may have any one of a variety of substituents, in replacement, for example, of one or more hydrogen atoms in the compound, or may have no substituents. Functional groups according to the invention include but are not limited to halogen (Cl, Br, F), hydroxyl (OH), thiol (SH), keto (C=O), carboxyl (COOH), ethers, thioethers, amidine (C(=NH)NR$_3$R$_4$, guanidine (NHC(=NH)NR$_3$R$_4$, glutamyl CH(NR$_3$R$_4$) (C(=O)OR$_5$), nitrate (ONO$_2$), nitro (NO$_2$), nitrile (CN), trifluoromethyl (CF$_3$), trifluoromethoxy (OCF$_3$), O-alkyl, S-alkyl, NH-alkyl, N-dialkyl, O-aralkyl, S-aralkyl, NH-aralkyl, amino (NH$_2$), azido (N$_3$), hydrazino (NHNH$_2$), hydroxylamino (ONH$_2$), sulfoxide (SO), sulfone (SO$_2$), sulfide (S—), disulfide (S—S), silyl, heterocyclic, alicyclic and carbocyclic. Preferred substituents include halogens, alcohols and ethers (OR$_1$), thiols and thioethers (SR$_2$), amines (NR$_3$R$_4$), amidines [C(=NH)NR$_3$R$_4$], guanidines [NHC(=NH)NR$_3$R$_4$], aldehydes (CH=O), acids [C(=O)OH], esters [C(=O)OR$_5$], amides [C(=O)NR$_3$R$_4$] and glycine [CH(NH$_2$) (C(=O)OH)].

The above groups Y and T can be referenced as "letters." The use of such terminology reflects the fact that the different functional groups on the phosphoramidate and phosphorothioamidate moieties are positioned in sequences (either predetermined or by random selection) much like letters of the alphabet—thus the term "letter." These letters can be "reactive" or "non-reactive." By reactive, it is meant that they will interact with a target molecule in some manner (that need not but can be predefined). By non-reactive, it is meant that they are not designed to primarily interact with a target molecule, and in fact while they may interact with the target molecule, the primary purpose of the non-reactive moieties are to impart other properties to the molecule such as, but not necessary limited to, effecting up-take, distribution, metabolism or identification.

Reactive functionalities used as letters, suitable for use in the practice of this invention include, but are not limited to, halogens; substituted or unsubstituted heterocyclic compounds, such as substituted or unsubstituted heterocycloalkyls; amino containing groups, such as heterocycloalkylamines, polyalkylamines, imidazoles, imadiazole amides, alkylimidazoles; substituted or unsubstituted aldehydes; substituted or unsubstituted ketones; substituted or unsubstituted ethers; substituted or unsubstituted esters; substituted or unsubstituted aryl compounds having from about 6 to about 20 carbon atoms, such as aralkylamino having from about 6 to about 20 carbon atoms, aminoaralkylamino having from about 6 to about 20 carbon atoms, alkyloxyaryl compounds, or allyloxyaryl compounds.

The functional groups are attached to the phosphoramidate or phosphorothioamidate moieties with or without intervening tethers. Tethers as used in the context of this invention are bivalent groups that have a primary or secondary amine or other suitable group to react with an H phosphonate or H phosphonothioate of the invention and a second functional group capable of binding a letter. Such tethers can be used to position "letters" in space with respect to the phosphoramidate backbone or to link letters that themselves do not include an amine group—necessary to form a phosphoramidate linkage—as an inherent part of the letter. A particularly preferred group of compound, when substituted with an appropriate amine functional group where necessary, useful as tether include, but are not limited to, C$_2$–C$_{10}$ alkyl, C$_2$–C$_{10}$ alkenyl, C$_2$–C$_{10}$ alkynyl, C$_4$–C$_7$ carbocylo alkyl or alkenyl, heterocycles, an ether having 2 to 10 carbon atoms and 1 to 4 oxygen or sulfur atoms, polyalkyl glycols and C$_7$–C$_{14}$ aralkyl groups.

Amines include amines of all of the above alkyl, alkenyl and aryl groups including primary and secondary amines and "masked amines" such as phthalimide. Amines of this invention are also meant to include polyalkylamino compounds and aminoalkylamines such as aminopropylamines and further heterocycloalkylamines, such as imidazol-1, 2, or 4-yl-propylamine.

Other reactive functionalities suitable for practicing the invention include, without limitation, compounds having thiol (SH), aldehyde (C=O), or alcohol (OH) functionalities.

Heterocycles, including nitrogen heterocycles, suitable for use as functional groups include, but are not limited to, imidazole, pyrrole, pyrazole, indole, 1H-indazole, α-carboline, carbazole, phenothiazine, phenoxazine, tetrazole, triazole, pyrrolidine, piperidine, piperazine and morpholine groups. A more preferred group of nitrogen heterocycles includes imidazole, pyrrole, and carbazole groups. Imidazole groups are especially preferred.

Purines and pyrimidines suitable for use as functional groups include adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch, et al., *Angewandte Chemie, International Edition* 1991, 30, 613.

Aryl groups according to the invention include but are not limited to substituted and unsubstituted aromatic hydrocarbyl groups such as phenyl and naphthyl groups. Aralkyl groups include but are not limited to groups having both aryl and alkyl functionality, such as benzyl and xylyl groups.

Metal coordination groups according to the invention include but are not limited to hydroxamic acids, catecholamide, acetylacetone, 2,2'-bipyridine, 1,10-phenanthroline, diacetic acid, pyridine-2-carboxamide, isoalkyldiamine, thiocarbamate, oxalate, glycyl, histidyl and terpyridyl. Other metal coordination groups are known, as for example see Mellor, D. P., *Chemistry of Chelation and Chelating Agents in International Encyclopedia of Pharmacology and Therapeutics*, Section 70, The Chelation of Heavy Metals, Levine, W. G. Ed., Pergamon Press, Elmford, N.Y., 1979.

Non-reactive functionalities used as letters, such as groups that enhance pharmacodynamic properties, include groups that improve uptake, enhance resistance to degradation, and/or strengthen sequence-specific interaction with a target molecule. Non-reactive functionalities may also enhance pharmacokinetic properties, in the context of this invention, such groups improve uptake, distribution, metabolism or excretion. Non-reactive functionalities include, but are not limited to, alkyl chains, polyamines, ethylene glycols, polyamides, aminoalkyl chains, amphipathic moieties, points for reporter group attachment, and intercalators attached to any of the preferred sites for attachment, as described above.

Solid supports according to the invention include controlled pore glass (CPG), oxalyl-controlled pore glass (see, e.g., Alul, et al., *Nucleic Acids Research* 1991, 19, 1527), TentaGel Support—an aminopolyethyleneglycol derivatized support (see, e.g., Wright, et al., *Tetrahedron Letters* 1993, 34, 3373) or Poros—a copolymer of polystyrene/divinylbenzene.

A number of functional groups can be introduced into compounds of the invention in a blocked form and subsequently de-blocked to form a final, desired compound. In general, blocking groups render chemical functionality inert to specific reaction conditions and can be appended to and removed from such functionality in a molecule without substantially damaging the remainder of the molecule. See, e.g., Green and Wuts, Protective Groups in Organic Synthesis, 2d edition, John Wiley & Sons, New York, 1991. For example, amino groups can be blocked as phthalimido groups or as 9-fluorenylmethoxycarbonyl (FMOC) groups and carboxyl groups can be protected as fluorenylmethyl groups. Representative hydroxyl protecting groups are described by Beaucage, et al., *Tetrahedron* 1992, 48, 2223. Preferred hydroxyl protecting groups are acid-labile, such as the trityl, monomethoxytrityl, dimethoxytrityl, trimethoxytrityl, 9-phenylxanthine-9-yl (Pixyl) and 9-(p-methoxyphenyl) xanthine-9-yl (MOX).

In the compounds of the invention, as noted above, in certain embodiments E1 and E2 are selected as conjugate groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, phospholipids, biotin, phenanthroline, phenazine, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992, U.S. patent application Ser. No. 116,801, filed Sep. 3, 1993, and U.S. Pat. No. 5,218,105. Each of the foregoing is commonly assigned with this application. The entire disclosure of each is incorporated herein by reference.

In structure I, $E_1$ and $E_2$ are the ends of the oligomer which is m repeating units long. During synthesis, the ends are in fact working ends, e.g. can be used to link the structure to a solid support or the like and can be used to extend the oligomeric structures. The repeating units are the bracketed portions of structure I.

During solid phase synthesis, $E_1$ is selected to be an activated solid support and $E_2$ is selected to alternate, as the synthesis proceeds, between a protecting group or hydrogen. L, as noted above, is a space spanning group also referred to as a spanner unit. Y and T, alone or together with the nitrogen atom of the phosphoramidate or phosphorothioamidate moieties, form the functional groups of the compounds of the invention. Y is typically a hydrogen but can be a tethered or untethered, reactive or non-reactive functional group. T is hydrogen, a tethered or untethered functional group or together with Y form a nitrogen containing heterocycle about nitrogen. T and Y, independently or together, are the above defined "letters."

X is either oxygen or sulfur. When X is O, the compounds of the invention are identified as phosphoramidates. When X is S, the compounds are identified as phosphorothioamidates. In certain embodiments, each X will be O. In other embodiments, each X will be S. In other embodiments, mixtures of O and S are both included in a compound of the invention.

Oligomeric compounds of the invention can be synthesized with the sequence of letters predetermined or random. Thus in certain preferred embodiments, the sequence of letters is a predetermined sequence. In further preferred embodiments, the sequence of letters is random. In even further preferred embodiments, the sequence is modulated between fixed and random. This is especially useful, as for example, in certain combinatorial strategies such as the above referenced SURF strategy.

A further advantage of this invention is the ability to synthesize oligomeric compounds that, in addition to or in place of variability in the sequences of the letters, have an asymmetric sequence of spanner units. Stated otherwise, the spanner units can also vary within an oligomeric structure. This is easily accomplished by using different dehydrase compounds that eventually become incorporated as spanner units.

One preferred method of synthesizing the compounds of the invention is via a solid phase synthesis. Representative solid phase techniques are those typically employed for DNA and RNA synthesis utilizing standard phosphoramidite chemistry. (see, e.g., Protocols For Oligonucleotides And Analogs, Agrawal, S., ed., Humana Press, Totowa, N.J. 1993.)

A preferred solid phase synthesis utilizes H phosphonates and H phosphonothioates as activated phosphites. The chemistry of the phosphorous atom in H phosphonates and H phosphonothioates is $P^{III}$. The intermediate compounds are subsequently oxidized to the $P^V$ state in the presence of a primary or secondary amine attached to a letter. The letter is attached to a primary or secondary amine either with or without a tether. Certain nitrogen containing heterocycles are used as the attaching moiety wherein the nitrogen is covalently bound to phosphorous. In addition to solid phase synthesis, solution phase synthesis can also be utilized to synthesize the compounds of the invention. Solution phase chemistry is accommodated by attaching a base labile protecting group e.g. FMOC, TBDMS, or TPDMS to $E_1$.

The letters are attached to their respective phosphite groups to form the phosphoramidate and phosphorothioamidates of the invention. One preferred method of effecting this attachment is via oxidation. Oxidation of the H phosphonate or H phosphonothioate intermediates of the invention in the presence of functional groups attached with or without a tether to a primary or secondary amine will form the phosphoramidates or phosphorothioamidates. These functional groups thus provide diverse properties ("diversity") to the resulting oligomeric compounds. The functional groups include hydrogen-bond donors and acceptors, ionic moieties, polar moieties, hydrophobic moieties, aromatic centers, and electron-donors and acceptors. Together, the properties of the individual repeating units contribute to the uniqueness of the oligomer in which they are found. Thus, a library of such oligomers would have a myriad of properties, i.e., "diversity." Collectively, the properties of the repeating units that form an oligomer contribute to the uniqueness of such an oligomer and impart certain characteristics thereto for interaction with cellular, enzymatic or nucleic acid target sites.

The oligomeric compounds of the invention can be prepared having either preselected sequences or sequences determined via combinatorial strategies. One useful combinatorial strategy is the above-noted SURF strategy, which is disclosed and claimed in U.S. patent application Ser. No. 749,000, filed Aug. 23, 1991, and PCT Application US92/07121, filed Aug. 21, 1992, both of which are commonly assigned with this application. The entire disclosure of these applications are herein incorporated by reference.

Illustrative of the SURF strategy is a 2'-O-methyl oligonucleotide library (see, Ecker et. al., ibid.) shown in Table I, below. Table I describes the selection of a 2'-O-methyl oligonucleotide for binding to an RNA hairpin. The $K_D$'s, i.e., the binding constants, were determined by gel shift. "X" is used to indicate the position being varied and underlining is used to indicate positions that become fixed during successive iterations of the SURF strategy.

TABLE I

| Subsets | $K_D$ (mM) | | | |
|---|---|---|---|---|
| | X = A | X = C | X = G | X = T |
| Round 1 | | | | |
| NNNNXNNN | 22 | <u>10</u> | >100 | >100 |
| Round 2 | | | | |
| NNNNCNXNN | >10 | <u>4</u> | >10 | >10 |
| Round 3 | | | | |
| NNXNCNCNN | >10 | <u>0.5</u> | >10 | >10 |
| Round 4 | | | | |
| NNCXCNCNN | >10 | <u>0.15</u> | >10 | >10 |

TABLE I-continued

| Subsets | $K_D$ (mM) | | | |
|---|---|---|---|---|
| | X = A | X = C | X = G | X = T |
| Round 5 | | | | |
| NNCCCXCNN | <u>0.08</u> | >1 | 0.4 | >1 |
| Round 6 | | | | |
| NNCCCACXN | <u>0.05</u> | >0.5 | 0.08 | >0.5 |
| Round 7 | | | | |
| NXCCCACAN | >0.1 | >0.1 | <u>0.03</u> | >0.1 |
| Round 8 | | | | |
| NGCCCACAX | 0.05 | <u>0.02</u> | 0.05 | 0.04 |
| Round 9 | | | | |
| XGCCCACAC | 0.03 | 0.05 | 0.02 | <u>0.01</u> |

This SURF strategy has not been previously used for libraries except those that employ naturally-occurring nucleotides as phosphodiesters or phosphorothioates as monomeric units. Other combinatorial strategies have only been previously used for libraries that employ amino acids as monomeric units.

One aspect of the present invention is the inclusion of oligomeric structures of the invention having the above structure in the above-described SURF strategy. The functional groups appended to these oligomeric structures can be incorporated into libraries while retaining the advantages of automated phosphoramidate or phosphorothioamidate oligomer synthesis. These functional groups can effect interactions of the following types: hydrogen-bond donor and acceptor, ionic, polar, hydrophobic, aromatic, and electron donors and acceptors. Preferred functional groups include aminoethyl, carboxyethyl, adenylmethyl, thyminylmethyl, imidazolylmethyl, benzyl, myristyl, isopropyl, and tetraethylene glycol groups.

One advantage of the present invention is that the simple design of repeating units enables combining rational drug design with screening mechanisms for thousands of compounds. This is achieved by using the compounds of the invention in a combinatorial techniques such as the SURF strategies. A preferred target molecule for utilizing such combinatorial techniques is the phospholipase $A_2$ family.

Phospholipases $A_2$ ($PLA_2$) are a family of enzymes that hydrolyze the sn-2 ester linkage of membrane phospholipids resulting in release of a free fatty acid and a lysophospholipid (see, Dennis, E. A., The Enzymes, Vol. 16, pp. 307–353, Boyer, P.D., ed., Academic Press, New York, 1983). Elevated levels of type II $PLA_2$ are correlated with a number of human inflammatory diseases. The $PLA_2$-catalyzed reaction is the rate-limiting step in the release of a number of pro-in-flammatory mediators. Arachidonic acid, a fatty acid commonly linked at the sn-2 position, serves as a precursor to leukotrienes, prostaglandins, lipoxins and thromboxanes. The lyso- phospholipid can be a precursor to platelet-activating factor. $PLA_2$ is regulated by pro-inflammatory cytokines and, thus, occupies a central position in the inflammatory cascade (see, e.g., Dennis, ibid.; Glaser, et al., TiPs Reviews 1992, 14, 92; and Pruzanski, et al., Inflammation 1992, 16, 451).

All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath, et al., *Inflammation* 1988, 12, 549) or into the articular space of rabbits (Bomalaski, et al., *J. Immunol.* 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g., pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott, et al., *Science* 1990, 250, 1541). Recently, the crystal structure of $PLA_2$ from human synovial fluid has been solved (Wery, et al., *Nature* 1991, 352, 79). The structures clarify the role of calcium and amino acid residues in catalysis. The calcium acts as a Lewis acid to activate the scissile ester carbonyl of 1,2-diacylglycerophospholipids and bind the lipid, and a His-Asp side chain dyad acts as general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site. (see, e.g., Achari, et al., *Cold Spring Harbor Symp. Quant. Biol.* 1987, 52, 441; Cho, et al., *J. Biol. Chem.* 1988, 263, 11237; Yang, et al., *Biochem. J.* 1989, 262, 855; and Noel, et al., *J. Am. Chem. Soc.* 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. The evidence favoring this hypothesis comes from studies revealing that rapid changes in $PLA_2$ activity occur concurrently with changes in the fluorescence of a membrane probe (Burack, et al., *Biochemistry* 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger, et al., *FEBS Lett.* 1989, 252, 73). These studies clearly show that $PLA_2$ binds exclusively at the boundary region between liquid and solid phase lipid.

While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e., phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (see, e.g., Yuan, et al., *J. Am. Chem. Soc.* 1987, 109, 8071; Lombardo, et al., *J. Biol. Chem.* 1985, 260, 7234; Washburn, et al., *J. Biol. Chem.* 1991, 266, 5042; Campbell, et al., *J. Chem. Soc., Chem. Commun.* 1988, 1560; and Davidson, et al., *Biochem. Biophys. Res. Commun.* 1986, 137, 587), reports describing in vivo activity are limited (see, e.g., Miyake, et al., *J. Pharmacol. Exp. Ther.* 1992, 263, 1302).

In one preferred embodiment, functional groups appended to the repeating units of the invention are selected for their potential to interact with, and preferably inhibit, the enzyme $PLA_2$. Thus, the compounds of the invention can be used for topical and/or systematic treatment of inflammatory diseases including atopic dermatitis and inflammatory bowel disease.

In selecting the functional groups, advantage can be taken of $PLA_2$'s preference for anionic vesicles over zwitterionic vesicles. Further advantage can also be taken of the compounds of the invention having phosphate groups since the natural substrate of $PLA_2$ contains a phosphate group.

Certain compounds of the invention include aromatic functional groups to facilitate binding to the cleft of the $PLA_2$ enzyme. (see, Oinuma, et al., *J. Med. Chem.* 1991, 34, 2260; Marki, et al., *Agents Actions* 1993, 38, 202; and Tanaka, et al., *J. Antibiotics* 1992, 45, 1071). Benzyl and 4-hexylbenzyl groups are preferred aromatic groups. The compounds of the invention can further include hydrophobic functional groups such as tetraethylene glycol groups. Since the $PLA_2$ enzyme has a hydrophobic channel, hydrophobicity is believed to be an important property of inhibitors of the enzyme.

The $PLA_2$ assay can be effected using a combinatorial screening strategy such as the SURF strategy. For this assay, the oligomer libraries are screened for inhibition of human type II $PLA_2$ enzymatic activity. Typically, these libraries contain about 8000 different compounds. Successive iterations of the SURF technique is effected to select unique oligomers from the library. The libraries additionally can be screened in other in vitro assays to determine further mechanisms of inhibition.

To maximize the identification of a tight binding oligomeric inhibitor of $PLA_2$ via a combinatorial approach, an array of functional groups typically are included in a randomized library. The oligomers are assembled in a manner similar to oligonucleotide synthesis by the coupling of monomeric, H phosphonate and H phosphonothioate units followed by an oxidation step to attach the functional group. The region of space normally occupied only by nucleobases will be occupied by nucleobases in addition to other functional groups selected to provide different ligand-ligand interactions, than that provided by the nucleobases. The sugar moiety of a normal nucleotide is replaced by a phosphoramidate or phosphorothioamidate, to form a unique phosphoramidate or phosphorothioamidate backbone. This methodology provides for a convergent preparation of a large number of monomers bearing a wide variety of functional groups. Where necessary, functional groups are protected with base labile protecting groups to allow one-step deprotection of the oligomer upon completion of the synthesis.

In certain embodiments of the invention, repeating units are incorporated into libraries of oligomeric compounds and increasingly less complex subsets of oligomers are identified in combinatorial screening techniques such as the above-described SURF technique by successive rounds of screens. In one preferred embodiment of the invention the spanner units are held fixed and the functional group is randomized. In another preferred embodiment of the invention the functional group is held fixed and the spanner unit length is randomized. In another preferred embodiment of the invention the functional group and the spanner unit length are randomized simultaneously. In a more preferred embodiment of the invention a combinatorial library is prepared wherein the spanner unit is held fixed and the functional group is randomized. Upon identification of an active oligomer in a first phase of screening the letters of the most active oligomer are further modified. For example, if a first phase of screening results in an active compound that contains a benzyl group, then in a subsequent second phase of screening the activity of this compound will be compared to that of compounds containing modifications to this aromatic ring e.g. the effect of substitutions. In a third phase of screening the effect of randomizing spanner units is studied. In this way, structural activity is identified in a stepwise manner to define increasingly more potent inhibitors of the enzymatic activity.

To detect an active sequence generated via a combinatorial technique, the concentration of the active molecule selected should be sufficiently great such that the molecule can be detected within the sensitivity of the chosen assay. As will be recognized, the number of unique oligomer sequences within a subset produced via a combinatorial technique depends on the length of the oligomer and the number of different repeating units employed. The number of sequences can be determined by raising the number of repeating units to a power equal to the number of random positions. This is illustrated in Table II. Table II also indicates the concentration of each sequence when the subset concentration is 100 μM, a typical high-test concentration. As a first approximation, the number of repeating units and their length can be based upon an estimate of the expected $IC_{50}$ (i.e., a concentration at which 50% of enzyme activity is inhibited) that is desirable in a final oligomeric compound. For an expected $IC_{50}$ of 100 nM, the complexities shown in Table II are acceptable, that is, the libraries shown in Table II have complexities that would allow detection of a unique sequence with an $IC_{50}$ of about 100 nM or less.

TABLE II

| Length | Complexity of Libraries | |
|---|---|---|
| | Sequences Per Subset | nM Each Sequence At 100 μM Subset |
| 5 Monomers | | |
| 4-mer | 125 | 800 |
| 5-mer | 625 | 160 |
| 6 Monomers | | |
| 4-mer | 216 | 463 |

TABLE II-continued

| Length | Complexity of Libraries | |
|---|---|---|
| | Sequences Per Subset | nM Each Sequence At 100 μM Subset |
| 5-mer | 1,296 | 77 |
| 7 Monomers | | |
| 4-mer | 343 | 291 |
| 8 Monomers | | |
| 4-mer | 512 | 195 |
| 10 Monomers | | |
| 4-mer | 1,000 | 100 |

If five letters are selected for a library consisting of uniform spanner unit length, then the library will have a length of five repeating units and one spanner unit, and will be substituted with letters XNNNN, where N is an equal molar mixture of letters and X is a different letter in each of the five subsets. For ease of synthesis, the fixed position can be selected as the right end of the molecule. After assay for inhibition of $PLA_2$ activity as described below, position X is fixed with the letter giving the greatest inhibition and the next subset is synthesized and screened. The fixed position then shifts towards the left end of the oligomer as unrandomization proceeds. Five rounds of synthesis and screening are required to determine a unique inhibitor.

The repeating units of the invention are linked to form oligomeric compounds using standard H phosphonate chemistry and in a like manner, H phosphonothioate chemistry, as has been used for synthesis of oligonucleotides. In one embodiment of the invention, since the coupling rates of letters will vary, the reactivity of the individual letters is adjusted such that equal molar incorporation of each letter at each randomized position is effected. A technique for optimizing such adjustment is disclosed in the United States patent application entitled "Random Oligonucleotide Libraries And Methods Of Making The Same," Ser. No. 08/1179, 972, filed Jan. 11, 1994—also identified as attorney docket number ISIS-1009. The foregoing patent application is commonly assigned, and is incorporated herein by reference.

In a SURF screening strategy the amount of oligomer is selected such that the concentration of each subset in the initial round of screening is relatively high (about 100 μM). It is presently preferred to synthesize oligomers using a DNA synthesizer. On such synthesizers the oligomers are most conveniently synthesized on a 1 to 4 μmol scale. Given the concentration of a subset of libraries at about 100 μm, the assays preferably are performed in a small volume of less than about 200 μL.

In the above noted Structure I, repeating units (in brackets) can be linked with one another to form homopolymeric structures or they can be linked with nucleosides and/or other moieties to form heteropolymeric structures. For example, chimeric structures can be formed that include one or more regions or "stretches" of the monomeric units of the invention joined to one or more regions or "stretches" of naturally occurring or synthetic oligonucleotides or to other synthetic or natural oligomeric compounds such as peptides, peptoids, peptide nucleic acids, oligo and/or polysaccharides. Further, oligomeric compounds having structure I can be incorporated into chimeric structures along with the compounds disclosed in the patent application entitled "Monomeric Diols And Phosphate Linked Oligomers Formed Therefrom," Ser. No. 08/1179,970, filed Jan. 11, 1994, also identified as attorney docket ISIS-0868 and the patent application entitled "Oligonucleotide Mimics Having Nitrogen-Containing Linkages," Ser. No. 08/180, 124, filed Jan. 11, 1994, also identified as attorney docket ISIS-1014. The foregoing patent applications are filed concurrently with this application, are commonly assigned, and are incorporated herein by reference.

In one embodiment of the invention, oligomeric compounds are synthesized as shown in Structure I having a fixed, predetermined sequence of "letters." In a further embodiment of the invention, oligomeric compounds are synthesized as shown in Structure I having random sequences. Further libraries of such randomly sequenced compounds can be prepared. This synthetic strategy emphasizes attachment of widely different functional groups to a variable phosphoramidate or phosphorothioamidate backbone to form the members of the library.

In one embodiment of the invention functional groups are appended to a phosphoramidate or a phosphorothioamidate diester oligomer. A spanner unit having two hydroxyl groups is protected using standard conditions (*Oligonucleotide Synthesis, A Practical Approach*, Gait. M. J., Ed., IL: New York., 1984, Chapter 1) with a dimethoxytrityl group or other suitable blocking group at one of the hydroxyls. This protected spanner unit is further reacted with succinic anhydride to form the protected spanner succinyl monoester. This monoester is activated with a leaving group e.g. pentafluorophenol or para nitrophenol, and derivatized onto a solid support e.g. LCAA CPG following standard methods,(M. J. Gait, ibid., Masad J. Damha, *nucleic acids research*, 1990, 18, 3813–3821). A capping step is performed using acetic anhydride to cap any remaining reactive sites. The DMT protecting group is removed with a dilute acid solution e.g. dichloroacetic acid or trichloroacetic acid thereby forming the deblocked spanner unit attached to solid support.

An H phosphonate mono ester-protected spanner unit is prepared by reacting a protected spanner unit with $PCl_3$ in the presence of imidazole or other suitable base following standard methods (*Nucleic Acids in Chemistry and Biology*; Blackburn, G. M., Gait M. J., Eds. Chemical Synthesis; IL: New York, 1990, Chapter 3, p. 98) to form a protected H phosphonate. The protected H phosphonate is isolated as a salt e.g. triethyl-ammonium or DBU salt (Froehler, B., et. al., *Nucleic Acids Research*, 1988, 16, 4831–4838). The resulting protected H phosphonate repeating unit, as a salt, is condensed onto the deblocked spanner unit attached to solid support to form the H phosphonate diester which is bound to solid support at one spanner unit and protected at the other spanner unit.

The H phosphonothioate diester is prepared by reacting a deblocked spanner unit attached to solid support prepared as above with bis(diisopropylamino)chlorophosphine in the presence of triethylamine or other suitable base following the method contained in U.S. Pat. No. 5,218,103 dated Jun. 8, 1993. The resulting intermediate is reacted with a protected spanner unit followed by treatment with hydrogen sulfide to form the H phoshponothioate diester which is bound to solid support at one spanner unit and protected at the other spanner unit.

A letter appended to a primary or secondary amine either with or without a tether is attached to the H phosphonate diester or the H phosphonothioate diester via oxidation thereby forming a phosphoramidate or a phosphorothioamidate. By repeating the above steps a phosphoramidate or a phosphorothioamidate backbone oligomeric structure can be prepared with a predetermined sequence of letters. Furthermore, using spanner units of different lengths and chemical complexity will add a second dimension to the diversity of the final compound. The resulting oligomeric compound is cleaved from the solid support using standard conditions e.g. ammonium hydroxide. Detritylation with dilute acid will yield the final oligomeric compound.

Modification of the above steps enable the synthesis of oligomeric structures of the invention with a fixed/random sequence of letters. Typically, an oligomeric structure is synthesized with one or more positions fixed and the other positions randomized. As testing proceeds, more positions are fixed and less are randomized until a unique compound is identified, Permutations of the above steps makes this possible.

To fix the first position or any number of positions starting from the solid support side of the compound the above steps are followed and the desired amine letter or letters are sequentially oxidized into the desired position as synthesis precedes. To randomize a single position with two or more amine letters, the selected letters are mixed together and the compound is oxidized with this mixture. To randomize two or more positions the oxidation step is omitted during that portion of the synthesis and these positions are oxidized in one step using a mixture of amine letters in the same manner as for one position e.g. more than one position can be oxidized simultaneously.

The concentration of individual amine letters in a mixture used for the oxidation step is adjusted for reactivity to ensure equal molar concentration in the final oligomer. To calculate the percentage of individual amine letters in an oligomeric structure it is necessary synthesize a test oligomeric compound using predetermined amine letters in equal molar amounts. The letters are cleaved from this oligomer with 10% formic acid at 50°–70° C. and analyzed by HPLC. The concentration of individual letters can be estimated from their known molar absorptivity. Alternatively, reaction of the oligomeric structure with phthalaldehyde and 2-thiolacetic acid will yield indole derivatives with high molar absorptivities (Bruckner, R., et al., *J. Chromatography*, 1989, 476, 73). This procedure has its greatest utility in those cases where the amine letter is not a UV-chromophore.

An alternative method of randomization is to effect the randomization one position at a time during the synthesis of the oligomeric compound. The solid support is divided into equal portions to coincide with the number of amine letters that are being used for randomization. Each portion of the solid support is treated with a different letter separately. The solid support is recombined and another repeating unit is added and the method is repeated until all the selected positions are randomized. The solid support is recombined for further synthesis. This method is referred to as bead splitting or resin splitting.

In certain combinatorial strategies, e.g. SURF, ibid, one letter is held fixed and the remaining positions are randomized. If the desired oligomer is a six mer—an oligomeric compound six units long—six oligomers are synthesized. The oligomers are synthesized on a DNA synthesizer in six separate runs. Each oligomer has one of six letters held fixed in the first position of the oligomer and the remaining positions are treated all at once with a mixture of the other five letters. As mentioned above the concentration of individual letters in a mixture is preadjusted with respect to reactivity to ensure equal molar ratios in each position on the oligomer. Alternatively, using bead splitting, the solid support can be separated into amounts equal to the number of letters in the mixture of letters and treated with each letter separately. This is done for each of the six libraries being prepared. When all the positions are randomized, the six resulting libraries of oligomers are tested in the assay of interest, as for example the above described $PLA_2$ assay, and the most active is determined. The oligomer that shows the most activity in this first round is chosen for a second round. In the second round the first position of all oligos is fixed with the letter that showed the most activity in round one. The second position is now fixed with the six letters as with the first run and the technique is repeated. Eventually a compound is identified from the last round where there are only six different oligomers in six assays.

In addition to randomizing letters, this invention also allows for variability in the spanner units. The spanner units as seen in Structure I above, are used to connect the phosphoramidate or phosphorothioamidate moieties of the invention. The spanner units thus "flank" the phosphoramidate or phosphorothioamidate moieties of the invention. In the preferred embodiments of the invention, the precursor to the spanner unit is a dehydrase compound—the simplest being ethylene glycol. Using different spanner unit precursors, e.g. propylene glycol, butylene glycol or higher homologues, during oligomer synthesis will change the distance between phosphoramidate or phosphorothioamidate moieties lending a further level of diversity to the compounds of the invention.

The spanner unit can also contain functional groups that enhance the pharmacologic and other activities. More sophisticated units are envisioned to be within the scope of this specification, e.g. 3-methoxy-1-2-propanediol. This variability adds a new dimension to the term randomization when compared to the current state of the art. When an active compound is identified and the functional groups are modified to maximize the activity, then spanner modification can be examined to further enhance the desired properties. This can be accomplished by modifying the synthesis of the phosphoramidates or phosphorothioamidate compounds simply by using different spanner unit precursors.

Oligomeric units bearing functional groups are prepared as per procedures described in the below examples. Reactive functional groups are appropriately blocked where necessary with a protecting group. Protecting groups are then removed upon completion of the synthesis of the oligomeric compound. Normally base labile protecting groups are used that are cleaved when the oligomer is removed from the resin.

EXAMPLE 1

2-O-(Dimethoxytrityl)ethanol

A solution of ethylene glycol (2.45 ml, 44 mmol) in dry pyridine (25 ml) was cooled to 0° C. in an ice bath. Excess triethylamine (7 ml) and 4-dimethylaminopyridine catalyst (120 mg, 1 mmol) was added followed by the slow addition of dimethoxytrityl chloride (7.42 g, 21.9 mmol) over 30 minutes. The mixture was stirred at 0° C. for 1 hr and then room temperature for 1 hr. The resulting solution was quenched with methanol and evaporated to dryness under reduced pressure. The residue was dissolved in saturated $NaHCO_3$ and extracted with EtOAc. The EtOAc extracts were washed with cold saturated sodium bicarbonate and brine. The organic phase is separated, dried over sodium sulfate, filtered and evaporated under reduced pressure. The resulting residue is purified by flash column chromatography on silica gel using ethyl acetate-hexanes (gradient 10 to 20%). The title compound was isolated to yield 5.53 g (70%). $^1H$ NMR: ($CDCl_3$) δ 7.50–7.20, 6.90–6.80 (m, 13 H, ArH), 3.80 (s, 6 H, $OCH_3$), 3.75 (t, 2 H, $CH_2OH$), 3.25 (t, 2 H, $DMTOCH_2$).

EXAMPLE 2

2-O-(Dimethoxytrityl)ethoxyphosphonic Acid

A solution of imidazole (4.29 g, 63 mmol)in dry acetonitrile at 0° C. (100 ml) was treated dropwise with $PCl_3$ (1.77 ml, 20.3 mmol) over a period of 30 minutes. The resulting solution is further treated with triethylamine (9.06 ml, 65 mmol). To the thick slurry was added 2-O-(dimethoxytrityl)ethanol (2.10 g, 5.81 mmol) in anhydrous acetonitrile (150 ml) slowly over a period of 30 minutes. The mixture is allowed to warm to room temperature and stirred for 15 minutes. The mixture is quenched with 1M TEAB and the mixture is evaporated in vacuo to a minimum volume and extracted with dichloromethane (2×150 ml). The dichloromethane extracts are washed with TEAB and evaporated in vacuo. The residue was purified by flash column chromatography using a gradient of 0% to 5% methanol in dichloromethane/1% triethylamine to yield 1.3 g purified material (43%). $^1H$ NMR: ($CDCl_3$) δ 7.50–7.20, 6.90–6.80 (m, 13 H, ArH), 6.96 (d, 1 H, $J_{PH}$=624 Hz, PH), 4.06 (m, 2 H, $CH_2OP$), 3.80 (s, 6 H, $OCH_3$), 3.25 (t, 2 H, $DMTOCH_2$), 3.05 (q, 6 H, $N(CH_2CH_3)_3$), 1.25 (t, 9 H, N $(CH_2CH_3)_3$). $^{31}P$ NMR ($CDCl_3$); 5.89.

EXAMPLE 3

Synthesis of 2-O-(Dimethoxytrityl)-ethylsuccinate Half Ester

A solution of 2-O-(dimethoxytrityl)ethanol (1.0 g, 2.77 mmol), triethylamine (0.4 ml, 3 mmol), and 4-dimethylamino-pyridine catalyst (120 mg, 1 mmol) in dry dichloroethane was treated with succinic anhydride (410 mg, 0.41 mmol). The mixture was stirred at 50° C. for 1.5 hr and then cooled to room temperature. The mixture was kept at room temperature for 16 hrs. The mixture is filtered and the filtrate was purified by silica gel flash column chromatography using chloroform:methanol-triethylamine to yield the title compound as a triethylammonium salt. $^1H$ NMR: ($CDCl_3$) δ 7.50–7.20, 6.90–6.80 (m, 13 H, ArH), 4.26 (t, 2 H, $CH_2OCO$), 3.80 (s, 6 H, $OCH_3$), 3.25 (t, 2 H, $DMTOCH_2$), 3.05 (q, 6 H, $N(CH_2CH_3)_3$), 2.70 (m, 4 H, $OOCCH_2CH_2COO$), 1.25 (t, 9 H, $N(CH_2CH_3)_3$.

EXAMPLE 4

Derivatization of LCAA CPG with 2-O-(Dimethoxytrityl)-ethylsuccinate Half Ester

2-O-(Dimethoxytrityl)ethylsuccinate half ester triethylammonium salt (135 mg) was dissolved in dichloromethane (5 ml). 4-Dimethylaminopyridine catalyst (40 mg, 0.2 mmol) was added followed by toluene diisocyanate (0.029 ml, 0.2 mmol). The mixture was shaken for 18 min. Long chain alkyl amine controlled pore glass (LCAA CPG) (1.0 g) was added and the mixture was shaken with the exclusion of light for 16 hrs. The mixture was filtered and washed with dichloromethane and then diethylether (3×10 ml each). The CPG was shaken for 16 hrs in pyridine/water (4:1), filtered, and rinsed with pyridine (5×5 ml). A 10 mg of the dried CPG was treated with 3% trichloroacetic acid in dichloromethane. The presence of the trityl ion qualitatively verified the derivatization. The loading was measured to be 30 μmol/g by measuring the absorbance of the dimethoxytrityl cation.

EXAMPLE 5

Oligomer Synthesis Via Sequential Coupling of 2-O-(Dimethoxytrityl) ethoxy-phosphonic Acid to the Derivatized CPG of Example 4

The dimethoxytrityl protecting group of the derivatized resin in Example 4 is removed by a treatment with 2% dichloro-acetic acid followed by washing with dry acetonitrile. The resin is then washed with acetonitrile-pyridine (4:1) followed by a simultaneous treatment of the CPG with 20–30 equivalents of 2-O-(dimethoxytrityl)ethoxy-phosphonic acid and 20–30 equivalents of adamantane carbonyl chloride in acetonitrile-pyridine. The mixture is agitated by circulating the reagents in the synthesis vessel for 10–15 minutes. The CPG is then briefly washed with acetonitrile-pyridine and then treated with diisopropyl phosphite adamantane carbonyl chloride to cap all unreacted hydroxyl groups. Finally, the CPG is washed with acetonitrile-pyridine and then acetonitrile. An estimate of coupling efficiency is derived from the treatment of the oligomer with dichloracetic acid in acetonitrile followed by a measurement of the absorbance of an aliquot at 498 nm.

The CPG is treated with 2% dichloroacetic acid in acetonitrile and washed with dry acetonitrile. The CPG is then washed with acetonitrile-pyridine (4:1) followed by a simultaneous treatment of the CPG with 20–30 equivalents of the 2-O-(dimethoxytrityl)ethoxy-phosphonic acid and 20–30 equivalents of adamantane carbonyl chloride in acetonitrile-pyridine. The mixture is agitated by circulating the reagents in the synthesis vessel for 10–15 minutes. The CPG is then briefly washed with acetonitrile-pyridine and then treated with diisopropyl phosphite adamantane carbonyl chloride. Lastly, the CPG is washed with acetonitrile-pyridine and then acetonitrile to yield the derivatized CPG. An estimate of the second coupling may be made as above. Repeating the above procedure n times will yield an oligomer with n+1 spanner units and n H-phosphonate linkages which is tethered to a LCAA resin by a succinate group as described above.

EXAMPLE 6

Synthesis of 10-O-(Dimethoxytrityl)-1-decanol

A solution of decane-1,10-diol in dry pyridine and containing excess triethylamine is treated with one equivalent of dimethoxytrityl chloride for a period of six hours. The resulting solution is evaporated to dryness under reduced pressure, the residue redissolved in methylene chloride and the solution washed with cold saturated sodium bicarbonate, water and brine. The organic phase is separated, dried over sodium sulfate, filtered and again evaporated under reduced pressure. The resulting residue is flash-chromatographed on silica gel using ethyl acetate-hexanes to isolate the purified product. Characterization by H-NMR yields signals for the DMT group (multiplet, 8.0–7.0 ppm), the decane group (multiplets, 1.2–4.0 ppm) and the alcohol (variable).

EXAMPLE 7

Synthesis of 10-O-(Dimethoxytrityl)decyloxy-phosphonic Acid

A solution of three equivalents of imidazole in dry acetonitrile is treated dropwise with one equivalent of PCl3 over a period of 30 minutes. The resulting solution is further treated with excess triethylamine to drive the reaction to completion. After 1 hr the mixture is treated with a solution of one equivalent of 10-O-(dimethoxytrityl)decan-1,10-diol in dry acetonitrile and the mixture stirred at room temperature for an additional hour. This mixture is treated with an excess of a solution of triethylammonium bicarbonate, pH 8, to yield the title compound. The compound is purified by repeated extraction of the bicarbonate solution with ethyl acetate. Pooling and drying of the extracts over sodium bicarbonate followed by evaporation of the solvent under reduced pressure yields a compound which is used as such without further purification. Characterization by ³¹P NMR (doublet, 6 ppm, JP-H=600 Hz) and $^1$H NMR yields signals for the DMT and the decane groups as for 10-O-(dimethoxytrityl)decandiol and signals for the triethylammonium groups (doublet, triplet, 3.2–2.2 ppm).

EXAMPLE 8

Synthesis of 10-O-(Dimethoxytrityl)decylsuccinate Half Ester

A solution of 10-O-(dimethoxytrityl)decan-1,10-diol in dry dichloromethane is treated with one equivalent of succinic anhydride, excess triethylamine and 5 mole % of 4-dimethylaminopyridine catalyst. The mixture is stirred overnight under anhydrous conditions and then further diluted with dichloromethane. This solution is washed with cold, saturated sodium bicarbonate, water and brine. The solution is then dried over magnesium sulfate, filtered and evaporated to dryness under reduced pressure. The resulting solid is purified by silica gel flash column chromatography using ethyl acetate-methanoltriethylamine to yield the title compound as the triethylammonium salt. The free acid is obtained by repeated coevaporation of this material with wet methanol. Characterization by $^1$H NMR yields signals for the DMT and decylene groups as for 10-O-(dimethoxytrityl)decan-1,10-diol and signals for the succinic group (two closely spaced doublet of doublets, 2.5–3.0 ppm).

EXAMPLE 9

Derivatization of LCAA CPG with 10-O-(Dimethoxytrityl)decylsuccinate Half Ester

A commercially obtained sample of controlled pore glass derivatized with long chain alkylamine groups (LCAA CPG) is suspended in dry acetonitrile. In a separate dry container, 10-O-(dimethoxytrityl)decylsuccinate half ester is treated with two equivalents of pentafluorophenol, excess triethylamine and two equivalents of dicyclohexyl carbodiimide. The mixture containing activated 10-O-(dimethoxytrityl) decylsuccinate half ester is stirred under argon for one hour and then added to the suspension of CPG while maintaining anhydrous conditions. The mixture is then shaken gently for 6 hr, the supernatant is separated and the process is repeated twice more. The quantity of 10-O-(dimethoxytrityl) decylsuccinate half ester which is used in each treatment is based on the concentration of available amine groups per gram of LCAA CPG, generally found to be 25–40 mmoles/gram. The CPG is then treated with a dilute solution of acetic anhydride in pyridine for 1 hr to cap all unreacted amine functionalities and then washed several times with acetonitrile. The extent to which this CPG has been derivatized is determined by treating an accurately weighed sample of the resulting CPG with 2% dichloroacetic acid in acetonitrile and measuring the absorbance of an aliquot of the supernatant at 498 nm.

EXAMPLE 10

Oligomer Synthesis Via Sequential Coupling of 10-O-(di methoxytrityl)decyl-phosphonic Acid to the Derivatized CPG of Example 9

The dimethoxytrityl group of the derivatized CPG from Example 9 is removed by a treatment with 2% dichloroacetic acid followed by washing with dry acetonitrile. The CPG is washed with acetonitrile-pyridine (4:1) followed by a simultaneous treatment of the CPG with 20–30 equivalents of the 10-O-(dimethoxytrityl) decyl-phosphonic acid as the triethylammonium salt, 20–30 equivalents of adamantane carbonyl chloride in acetonitrile-pyridine. The mixture is agitated by circulating the reagents in the synthesis vessel for 10–15 minutes. The CPG is then briefly washed with acetonitrile-pyridine and then treated with diisopropyl phosphite adamantane carbonyl chloride to cap all unreacted hydroxyl groups. Finally, the CPG is washed with acetonitrile-pyridine and then acetonitrile. An estimate of coupling efficiency is derived from the treatment of the CPG with dichloracetic acid in acetonitrile followed by a measurement of the absorbance of an aliquot at 498 nm. Repeating the above procedure n times will yield an oligomer with n+1 decane units and n H-phosphonate linkages. The oligomer is tethered to a LCAA CPG by a succinate group as described above.

EXAMPLE 11

Oxidative Incorporation of Letters at H-Phosphonate Linkages
Method 1
Incorporation of Letters in Predetermined Sequence The solid support (e.g. LCAA CPG) is derivatized with a first spanner unit as per the procedure of Example 4 for an ethylene spanner unit or Example 9 for a decyl spanner unit. Next, the desired phosphonic acid monoester is condensed onto the derivatized solid support as per the procedure of Examples 5 and 10. The resulting phosphonic acid diester is reacted with a large molar excess of the amine letter next in the sequence. The amine letter is added in solution in carbon tetrachloride/pyridine. For the addition of two adjacent like letters in the oligomeric structure, the oxidation step is delayed until the backbone to support all of these letters is synthesized and all H phosphonate sites that will bear this letter are then oxidized simultaneously. (To improve the efficiency of incorporation of the letters into phosphoramidates or phosphorothioamidates, a coupling agent, i.e. 1-(3-dimethylaminopropyl)-3-ethylcarbodiimide hydrochloride (EDC) or dicyclohexylcarbodiimide (DCC) or triphenylphosphine, are added.) The solid support is shaken for 15 minutes and the supernatant is removed by filtration. The solid support is washed with pyridine. A second treatment with a large molar excess of the amine letter in carbon tetrachloride/pyridine followed by shaking will ensure efficient oxidation to the phosphoramidate. The above steps are repeated until all of the letter of the oligomer have been added. All letters are predetermined in this method of synthesis. Upon completion of the addition of the last of the desired length and configuration of oligomeric sequence, the solid support is washed with pyridine/acetonitrile and the phosphoramidate is cleaved from the resin by treatment with concentrated ammonium hydroxide at room temperature for 3 hours. Evaporation of the supernatant and purification of the phosphoramidate on an RP-18 HPLC column yields the final oligomer.

Method 2.
Incorporation of Letters in a Random Sequence

The method of oligomer synthesis as described in Examples 5 and 10 is repeated to synthesize the oligomer of desired length. To randomize the amine letters on the oligomer, the method of adding a letter as described in Method 1 above is followed except that, for randomization, the amine letters in carbon tetrachloride and a suitable cosolvent are added as a mixture. Random distribution of amine letters from this mixture of amine letters is verified experimentally by treatment of an oligomer, which has been previously treated with a mixture of amine letters and subsequently worked up and purified, with 10% aqueous formic acid at 50°–70° C. to release the amine letters. The actual percentages of incorporation of the individual amine letters is then determined by HPLC analysis of the reaction mixture and the relative individual rates are calculated. Having once determined the relative rates, in further iteration of the sequences, the concentration of amine letters within a mixture is adjusted to reflect these rate differences.

In a variation of this method of randomization, in a five mer all sites of which are to be randomized, the oxidation is effected simultaneously. The five mer backbone was synthesized as above and a mixture of the letters added. Upon completion of the backbone synthesis, the oxidation of amine letters is effected on all five sites as a single step.

In a further variation of this method of randomization, upon completion of the synthesis of the first backbone fragment, the resin is split into five portion and each portion is individual oxidized with one of the amine letter. The individual portions of the resin are recombined and the backbone is extended a further unit. The resin is then again split, and the individual portion each oxidized with one of the amine letter. This cycle is repeated to complete the synthesis.

Method 3
Incorporation of Amine Letters in Fixed/Random Sequence

Combining methods 1 and 2 above is used to fix certain positions while randomizing other positions as the oligomeric structure is synthesized. This method is further used in combination with a SURF combinatorial strategy.

EXAMPLE 12

Benzylamine Phosphoramidate Oligomer Synthesis

A solid support is derivatized with 2-O-(dimethoxytrityl) ethylsuccinate half ester as in Example 4. 2-O-(dimethoxytrityl) ethyl-phosphonic acid is condensed onto the derivatized resin as in Example 5. The above method of example 5 is repeated until six of the above phosphonic acid residues are incorporated. The resulting six mer is treated using the procedure of Example 11, Method 1, with a large excess of benzylamine in carbon tetrachloride/pyridine. The solid support is shaken for 15 minutes and the supernatant is removed by filtration and then washed with pyridine. A second treatment with a large excess of benzylamine in carbon tetrachloride/pyridine followed by shaking will insure efficient oxidation to the phosphoramidate. The resin is washed with pyridine/acetonitrile and then the phosphoramidate is cleaved from the resin by a treatment with concentrated ammonium hydroxide at room temperature for 3 hr. Evaporation of the supernatant and purification of the phosphoramidate on an RP-18 HPLC column will yield the final oligomer. The stepwise H phosphonate coupling efficiency is determined by measuring the absorbance of the trityl ion as described in Example 9.

EXAMPLE 13

Random Letter Phosphoramidate Oligomer Synthesis

The resin is derivatized with 2-O-(dimethoxytrityl)ethyl-succinate half ester as in Example 4, 2-O-(dimethoxytrityl) -ethyl-phosphonic acid is condensed with the derivatized resin as in Example 5. The above method of Example 5 is repeated until six of the above phosphonic acid residues have been incorporated. The resulting six mer is treated as per the procedure of Example 11, Method 2, with a large excess of an equal molar mixture of benzylamine, 2-(2-aminoethyl)-1-methylpyrrolidine, and piperonyl amine in carbon tetrachloride/pyridine. The resin is shaken for 15 minutes and the supernatant is removed by filtration and then washed with pyridine. A second treatment with a large excess of the mixture of amine letters in carbon tetrachloride/pyridine followed by shaking will insure efficient oxidation to the phosphoramidate. The resin is washed with pyridine/acetonitrile and then the phosphoramidate is cleaved from the resin by a treatment with concentrated ammonium hydroxide at room temperature for 3 hr. Evaporation of the supernatant and purification of the phosphoramidates on an RP-18 HPLC column will yield the final random oligomers. The stepwise H phosphonate coupling efficiency will be determined by measuring the absorbance of the trityl ion as previously described above.

EXAMPLE 14

Random Letter(s)/Fixed Letter(s) Phosphoramidate Oligomer Synthesis

The resin is derivatized with 2-O-(dimethoxytrityl)ethylsuccinate half ester as in Example 4, 2-O-(dimethoxytrityl)-ethyl-phosphonic acid is condensed with the derivatized resin as in Example 5. The above method of example 5 is repeated until 3 of the above phosphonic acid residues have been incorporated. The resulting trimer is treated as illustrated in Example 11, Method 2, with a large excess of a mixture of benzylamine, 2-(2-aminoethyl)-1-methylpyrrolidine, and piperonyl amine in carbon tetrachloride/pyridine. The resin is detritylated with trichloroacetic acid. The resin is treated with 2-O-(dimethoxytrityl)ethyl-phosphonic acid as in Example 5 and further treated as per the procedure of Example 11, Method 1 with benzylamine to fix position 4 in the growing oligomer. The resin is washed with pyridine/acetonitrile and then the phosphoramidate is cleaved from the resin by a treatment with concentrated ammonium hydroxide at room temperature for 3 hr. Evaporation of the supernatant and purification of the phosphoramidates on an RP-18 HPLC column yields the final random/fixed oligomers. The coupling efficiency is determined by measuring the absorbance of the trityl ion as described in Example 9.

EXAMPLE 15

Phosphoramidate Oligomeric Compounds with Fixed or Fixed/Random Letters and Further Containing Asymmetric Spanner Lengths Ethylene glycol is protected with dimethoxytrityl chloride as per the procedure of Example 1 and further reacted with succinic anhydride as per the procedure of Example 3. The resulting 2-O-(dimethoxytrityl)ethylsuccinate half ester is activated and derivatized onto LCAA CPG as per the procedure Example 4. 1,3-propanediol is protected with dimethoxytrityl chloride as per the procedure of Example 1 and further reacted with PCl3 as per the procedure of Example 2 to give 3-O-(dimethoxytrityl)propyl-phosphonic acid. The 3-O-(dimethoxytrityl)propyl-phosphonic acid is reacted with the 2-O-(dimethoxytrityl)ethylsuccinate derivatized LCAA CPG as per the procedure of Example 5 to give 3-O-(dimethoxytrityl)propoxy-[(2-O-succinyl-LCAA-CPG)-ethoxy]-H phosphonate. The 3-O-(dimethoxytrityl)propoxy-[(2-O-seconal-LCAA-CPG)-ethoxy]-H phosphonate is then treated with N-butylamine as per the procedure of Example 12 (except that the compound is kept attached to the resin) to give 3-O-(dimethoxytrityl) propoxy-[(2-O-succinyl-LCAA-CPG)-ethoxy]-N-butyl-phosphoramidate. 1,4-butanediol is protected with dimethoxytrityl chloride as per the procedure of Example 1 and further reacted with PCl$_3$ as per the procedure of Example 2 to give 4-O-(dimethoxytrityl)butyl-phosphonic acid. 3-O-(dimethoxytrityl)propoxy-[(2-O-seconal-LCAA-CPG)-ethoxy]-N-butyl-phosphoramidate is detritylated and further reacted with the 4-O-(dimethoxytrityl)butyl-phosphonic acid as per the procedure of Example 5 and further treated with N-propylamine as per the procedure of example 12. The resulting dimer is cleaved off the solid support using the procedure of Example 12, and purified by HPLC. The resulting oligomeric dimer is substituted at the two phosphoramidate nitrogens by N-butane and N-propane going from left to right. The phosphoramidate units are separated by a propane spanner unit and flanked on the left by an ethyl spanner unit and on the right by a butyl spanner unit. Substitution of a mixture of N-butylamine and N-propylamine for the N-propylamine above gives a two mer substituted with N-butane at position one and a random substitution of both N-butane and N-propane at position two.

EXAMPLE 16

[(2-O-seconal-LCAA-CPG)ethoxy]-bis(diisopropylamino)-phosphine

2-O-(Dimethoxytrityl)ethylsuccinate half ester derivatized solid support from Example 4, is detritylated using standard methods (e.g. 3% trichloroacetic acid) and further treated with bis(diisopropylamino)chlorophosphine as per Example III of U.S. Pat. No. 5,218,103 dated Jun. 8, 1993 to form a solid support bound (2-O-seconal)ethoxy-bis (diisopropylamino)phosphine.

EXAMPLE 17

2-O-Dimethoxytritylethoxy-[(2-O-seconal-LCAA-CPG)-ethoxy]-diisopropylaminophosphoramidite The 2-O-seconal)ethoxy-bis(diisopropylamino) phosphine from Example 16 is then treated with 2-O-(dimethoxytrityl)ethanol as per the procedure of Example III of U.S. Pat. No. 5,218,103 to give the title compound.

EXAMPLE 18

2-O-Dimethoxytritylethoxy-[(2-O-seconal-LCAA-CPG)-ethoxy]-hydrogenphosphonothioate 2-O-(Dimethoxytritylethoxy)-[(2-O-seconal-LCAA-CPG)-ethoxy)]-diisopropylaminophosphoramidite from Example 17 is treated with hydrogen sulfide and tetrazole as per the procedure of Example III of U.S. Pat. No. 5,218,103 to give the title compound.

EXAMPLE 19

2-O-Dimethoxytritylethoxy-[(2-O-seconal-LCAA-CPG)-ethoxy]-N-butylphosphorothioamidate 2-O-(Dimethoxytrityl)ethoxy-[(2-O-seconal-LCAA-CPG)-ethoxy]-hydrogenphosphonothioate from Example 18 is oxidized with I$_2$ in the presence of a selected amine letter, e.g butyl amine, utilizing the procedure of Example VI of U.S. Pat. No. 5,218,103 to give the title compound.

EXAMPLE 20

Oxidative Incorporation of Letters to Hydrogenphosphono-thioate (Random Sequences of Letters) General Methods Ethylene glycol is protected with dimethoxytrityl chloride as per Example 1 and further reacted with succinic anhydride as per Example 3. The resulting 2-O-(dimethoxytrityl) ethylsuccinate half ester is activated and derivatized onto LCAA CPG as per Example 4. Further treatment with bis(diisopropylamino)chlorophosphine as per the procedure of Example 16 gives the solid support bound ethoxy-bis (diisopropylamino)-phosphine. The solid support bound ethoxy-bis (diisopropylamino)-phosphine is reacted with 3-O-(dimethoxytrityl) propanol prepared as per the procedure of Example 1 to give 3-O-(dimethoxytrityl)propoxy-[(2-O-succinyl-LCAA-CPG)-ethoxy]-diisopropylaminophosphoramidite. The 3-O-(dimethoxytrityl)propoxy-[(2-O-succinyl-LCAA-CPG)-ethoxy]-diisopropylaminophosphoramidite is treated with hydrogen sulfide as per the procedure of Example 18 to give 3-O-(dimethoxytrityl)propoxy-[(2-O-succinyl-LCAA-CPG)-ethoxy]- diisopropylamino H phosphonothioate. The 3-O-(dimethoxytrityl)propoxy-[(2-O-succinyl-LCAA-CPG)-ethoxy]-diisopropylamino H phosphonothioate is treated with an equal molar mixture of N-butylamine and N-propylamine as per the procedure of Example 19 to give 3-O-(dimethoxytrityl)propoxy/butoxy-[(2-O-succinyl-LCAA-CPG)-ethoxy]-N-(N-butyl)-phosphorothioamidate. 1,4-butanediol is protected with dimethoxytrityl chloride as per the procedure of Example 1 and further reacted with bis(diisopropylamino)chlorophosphine as per the procedure of example 16 to give 4-O-(dimethoxytrityl)(butoxy-bis (diisopropylamino)-phosphine. The 3-O-(dimethoxytrityl)-propoxy-[(2-O-seconal-LCAA-CPG)-ethoxy]-N-(N-butyl)-phosphorothioamidate is detritylated as per the procedure of Example 16 and further reacted with the 4-O-(dimethoxytrityl)-butoxy-bis(diisopropylamino)-phosphine. Treatment with hydrogen sulfide as per the procedure of Example 18 gives the monosubstituted dimer. Treatment of the monosubstituted dimer with an equal molar mixture of N-butylamine and N-propylamine as per the procedure of Example 19 gives the disubstituted/randomized two mer. This is treated as per the procedure of Example 12 to cleave the oligomeric compound off the solid support. It is further purified by HPLC. The resulting oligomeric dimer is substituted at the two phosphorothioamidate nitrogens by N-butane and N-propane in an equal molar random distribution.

EXAMPLE 21

Phosphorothioamidate Oligomeric Compounds with Fixed or Fixed/Random Letters and Containing Symmetric Spanner Lengths Ethylene glycol is protected with dimethoxytrityl chloride as per Example 1 and further reacted with succinic anhydride as per Example 3. The resulting 2-O-(dimethoxytrityl) ethylsuccinate half ester is activated and derivatized onto LCAA CPG as per Example 4. Further treatment with bis(diisopropylamino)chlorophosphine as per the procedure of Example 16 gives the solid support bound ethoxy-bis (diisopropylamino)-phosphine. The solid support bound ethoxy-bis(diisopropylamino)-phosphine is reacted with 3-O-(dimethoxytrityl)propanol prepared as per the procedure of Example 1 to give 3-O-(dimethoxytrityl)propoxy-[(2-O-seconal-LCAA-CPG)-ethoxy]-diisopropylaminophosphoramidite. The 3-O-(dimethoxytrityl)propoxy-[(2-O-seconal-LCAA-CPG)-ethoxy]-diisopropylaminphosphoramidite. is treated with hydrogen sulfide as per the procedure of Example 18 to give 3-O-(dimethoxytrityl)-propoxy-[(2-O-seconal-LCAA-CPG)-ethoxy]-diisopropylamino H phosphonothioate. The 3-O-(dimethoxytrityl)propoxy-[(2-O-seconal-LCAA-CPG)-ethoxy]-diisopropylamino H phosphonothioate is treated with N-butylamine as per the procedure of Example 19 to give 3-O-(dimethoxytrityl)propoxy-[(2-O-seconal-LCAA-CPG)-ethoxy]-N-(N-butyl)-phosphorothioamidate. 1,4-butanediol is protected with dimethoxytrityl chloride as per the procedure of Example 1 and further reacted with bis (diisopropylamino)chlorophosphine as per the procedure of example 16 to give 4-O-(dimethoxytrityl)butoxy-bis (diisopropylamino)-phosphine. The 3-O-(dimethoxytrityl)propoxy-[(2-O-seconal-LCAA-CPG)-ethoxy]-N-(N-butyl)-phosphorothioamidate is detritylated as per the procedure of Example 16 and further reacted with the 4-O-(dimethoxytrityl)butoxy-bis(diisopropylamino)-phosphine. Treatment with hydrogen sulfide as per the procedure of Example 18 gives the monosubstituted two mer. Treatment of the monosubstituted two mer with N-butylamine as per the procedure of Example 19 gives the disubstituted two mer. Utilizing the procedure of Example 12, the oligomeric compound is cleaved off the solid support and purified by HPLC. The resulting oligomeric two mer is substituted at the two phosphorothioamidate nitrogens by N-butane and N-propane going from left to right. The phosphoramidate units are separated by a propane spanner unit and flanked on the left by an ethyl spanner unit and on the right by a butyl spanner unit. Substitution of a mixture of N-butylamine and N-propylamine for the N-propylamine above gives a two mer substituted with N-butane at position one and a random substitution of both N-butane and N-propane at position two.

EXAMPLE 22

Chimeric Oligomeric Structure

A fifteen-mer phosphorothioate-phosphoramidate-phosphorothioate chimeric compound is synthesized on an automated DNA synthesizer (Applied Biosystems model 380B) utilizing commercially available oligonucleotide reagents and compounds of the invention using standard phosphoramidite and phosphorothioate chemistries (see, Oligonucleotide Synthesis, A Practical Approach, M. J. Gait., ed., Oxford University Press, New York, 1990). The chimeric compound is synthesized in a standard 3 prime to 5 prime direction (e.g. 3 prime attached to solid support). The stepwise thiation of the phosphite linkage, to generate the phosphorothioate portion of the oligomer, is achieved utilizing a 0.2M solution of 3H-1,2,-benzodithiole-3-one 1,1-dioxide in acetonitrile. A five mer oligonucleotide phosphorothioate is synthesized using standard solid phase chemistry to give the oligonucleotide sequence TTTTT attached to a solid support. The five mer is further reacted with 2-O-dimethoxytrityl-ethyl-phosphonic acid (Example 2) as per the procedure of Example 5. The resulting H phosphonate is in the six position is oxidized with benzyl amine as per the procedure of Example 12. Positions 7 thru 10 are similarly substituted in a step wise manner by coupling with 2-O-dimethoxytrityl-ethyl-phosphonic acid followed by oxidation in the presence of benzylamine. The dimethoxytrityl group of the terminal spanner unit attached to the terminal phosphoramidate is removed using standard methods as in Example 5 and the remaining 5 nucleotides are incorporated using standard methods as above. Cleaving the fifteen mer off the solid support and deprotection of the DMT group in position 15 gives the fifteen mer.

EXAMPLE 23

$PLA_2$ Assay

The oligomer libraries are screened for inhibition of $PLA_2$ in an assay using E. coli labeled with $^3$H-oleic acid (see, Franson, et al., J. Lipid Res. 1974, 15, 380; and Davidson, et al., J. Biol. Chem. 1987, 262, 1698) as the substrate. Type II $PLA_2$ (originally isolated from synovial fluid), expressed in a baculovirus system and partially purified, serves as a source of the enzyme. A series of dilutions of each the oligomeric pools is done in water: 10 μl of each oligomer is incubated for 5 minutes at room temperature with a mixture of 10 μl $PLA_2$, 20 μl 5X $PLA_2$ Buffer (500 mM Tris 7.0–7.5, 5 mM $CaCl_2$), and 50 μl water. Each of the oligomer samples is run in duplicate. At this point, 10 μl of $^3$H E. coli cells is added. This mixture is incubated at 37° C. for 15 minutes.

The enzymatic reaction is stopped with the addition of 50 μl ₂M HCL and 50 μl fatty-acid-free BSA (20 mg/ml PBS), vortexed for 5 seconds, and centrifuged at high speed for 5 minutes. 165 μl of each supernate is then put into a scintillation vial containing 6 ml of scintillant (ScintiVerse) and cpms are measured in a Beckman Liquid Scintillation Counter. As a control, a reaction without oligomer is run alongside the other reactions as well as a baseline reaction containing no oligo as well as no PLA₂ enzyme. CPMs are corrected for by subtracting the baseline from each reaction data point.

EXAMPLE 24

Verification of Assay

The PLA₂ test system of Example 23 was verified using phosphorothioate oligonucleotides with one or more strings of guanosine nucleotides (at least 3 per string). Libraries of these oligonucleotides were deconvoluted using the SURFs screening strategy and were shown to have an inhibitory effect on the PLA₂ enzyme. Knowing that phosphorothioate oligonucleotides inhibit PLA₂ with some sequence specificity, an eight nucleotide phosphorothioate library consisting of the four natural bases was used to test the assay system for suitability as a SURF screen. This library had been synthesized for use in another system and all subsets were not still available (indicated by dashes in Table III, below). Using the SURF method, it was confirmed that a stretch of guanosines were necessary for inhibition of PLA₂ activity by the phosphorothioate oligonucleotide (Table III, below).

The assay was sensitive and accurate enough to discriminate between subsets of oligomers so that an inhibitory sequence could be selected. In each of the first three rounds of selection, the most active subset was readily determined. After 5 rounds, there was little difference in the activity of the subsets with at least 5 G's in a row, suggesting that the terminal positions are not critical for the inhibitory activity. The IC₅₀ of the "winner" improves (enzyme activity decreases) as more of the positions are fixed. As a test of the reproducibility of the assay, an eight nucleotide phosphorothioate oligonucleotide of a single sequence (TTGGGGTT) was assayed with each round of testing. This oligonucleotide acted as an internal control of the accuracy of the assay; the IC₅₀ was 8 μM in each assay.

TABLE III

| Inhibition of PLA₂ Activity by Library Subsets IC₅₀ (mM) | | | | |
|---|---|---|---|---|
| | X = A | X = G | X = C | X = T |
| Round 2 | | | | |
| NNGNXNNN | >50 | 25 | >50 | >50 |
| Round 3 | | | | |
| NNNGXGNNN | — | 10 | >50 | — |
| Round 4 | | | | |
| NNGGGXNN | 9 | 4 | 6 | 18 |
| Round 5 | | | | |
| NAGGGGXN | 4 | 2 | 4 | 4 |
| NGGGGGXN | 2.5 | 2 | 3 | 3 |
| NCGGGGXN | 5 | 4 | 5 | 5 |
| NTGGGGXN | 19 | 5 | 17 | 15 |

EXAMPLE 25

Assay of Library of Phosphoramidate and Phosphorothioamidate Oligomeric Compounds Against PLA₂

A first library containing phosphoramidate oligomeric compounds and a second library containing phosphorothioamidate oligomeric compounds is tested in the PLA₂ assay for identification of inhibitors of type II PLA₂. Confirmation of the "winners" is made to confirm that the oligomers binds to enzyme rather than substrate and that the inhibition of any oligomer selected is specific for type II PLA₂. An assay using $^{14}$C-phosphatidyl ethanolamine ($^{14}$C-PE) as substrate, rather than E. coli membrane, is used to insure enzyme rather than substrate specificity. Micelles of $^{14}$C-PE and deoxycholate are incubated with the enzyme and oligomer. $^{14}$C-labeled arachidonic acid released as a result of PLA₂-catalyzed hydrolysis is separated from substrate by thin layer chromatography and the radioactive product is quantitated. The "winner" is compared to phosphatidyl ethanolamine, the preferred substrate of human type II PLA₂, to confirm its activity. PLA₂ from other sources (snake venom, pancreatic, bee venom) and phospholipase C, phospholipase D and lysophospholipase can be used to further confirm that the inhibition is specific for human type II PLA₂.

EXAMPLE 26

Hybridization Probe for the Detection of Specific mRNA in Biological Sample

For the reliable, rapid, simultaneous quantification of multiple varieties of mRNA in a biological sample without the need to purify the mRNA from other cellular components, a mRNA of interest from a suitable biological sample, i.e., mRNA of a blood borne virus, a bacterial pathogen product in stool, urine and other like biological samples, is identified using standard microbiological techniques. An oligomeric compound of the invention having "nucleobase" functional groups (adenine, guanine, thymine and cytosine) complementary to the nucleic acid sequence of this mRNA is prepared as per the above examples. The oligomeric compound is immobilized on insoluble CPG solid support utilizing the procedure of Pon, R. T., Protocols for Oligonucleotides and Analogs, Agrawal, S., Ed., Humana Press, Totowa, N.J., 1993, p 465–496. A known aliquot of the biological sample under investigation is incubated with the insoluble CPG support having the oligomer thereon for a time sufficient to hybridize the mRNA to oligomer and thus to link the mRNA via the oligomer to the solid support. This immobilizes mRNA present in the sample to the CPG support. Other non-immobilized materials and components are then washed off the CPG with a wash media suitable for use with the biological sample. The mRNA on the support is labelled with ethidium bromide, biotin or a commercial radionucleotide and the amount of label immobilized on the CPG support is measured to indicate the amount of mRNA present in the biological sample.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound of the structure:

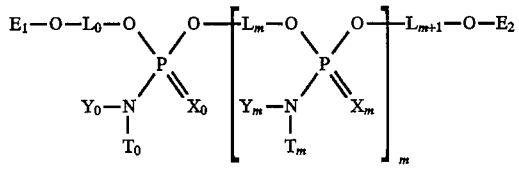

wherein:

$X_0$ and each $X_m$, independently, are O or S;

$Y_0$ and each $Y_m$, independently, are H, or $[Q_2]_j$—$Z_2$;

$T_0$ and each $T_m$, independently, are $[Q_1]_k$—$Z_1$, or together Y and T are joined in a nitrogen heterocycle;

$Q_1$, $Q_2$, $L_0$, $L_{m+1}$ and each $L_m$, independently, are $C_2$-$C_{10}$ alkyl, $C_2$-$C_{10}$ alkenyl, $C_2$-$C_{10}$ alkynyl, $C_4$-$C_7$ carbocylo alkyl or alkenyl, a heterocycle, a polyalkyl glycol, or $C_7$-$C_{14}$ aralkyl;

E1 and E2, independently, are H, a hydroxyl protecting group, an activated solid support, a conjugate group, a reporter group, a polyethylene glycol, alkyl, oligonucleotide, peptide nucleic acid, a phosphate, a phosphite, an activated phosphate, or an activated phosphite;

j and k independently are 0 or 1;

m is 1 to about 50;

$Z_1$ and $Z_2$, independently, are H, $C_1$-$C_2$ alkyl, $C_2$-$C_{20}$ alkenyl, $C_2$-$C_{20}$ alkynyl, $C_6$-$C_{14}$ aryl, $C_7$-$C_{15}$ aralkyl, CH=O, $OR_1$, $SR_2$, $NR_3R_4$, C(=NH)$NR_3R_4$, CH($NR_3R_4$), NHC(=NH)$NR_3R_4$, CH($NH_2$)C(=O)OH, C(=O)$NR_3R_4$, C(=O)$OR_5$, a metal coordination group, a reporter group, a nitrogen-containing heterocycle, a purine, a pyrimidine, a phosphate group, a polyether group, or a polyethylene glycol group;

$R_1$ is H, alkyl having 1 to about 6 carbon atoms, or a hydroxyl protecting group;

$R_2$ is H, alkyl having 1 to about 6 carbon atoms, or a thiol protecting group;

$R_3$ and $R_4$ are, independently, H, alkyl having 1 to about 6 carbon atoms, or an amine protecting group; and $R_5$ is H, alkyl having 1 to about 6 carbon atoms, or an acid protecting group.

2. The compound of claim 1 wherein $L_0$, $L_{m+1}$ and each $L_m$ are alkyl having from about 2 to about 10 carbons.

3. The compound of claim 1 wherein together $Y_m$ and $T_m$ are joined in a nitrogen heterocycle.

4. The compound of claim 3 wherein said heterocycle is piperidine or pyrrolidine.

5. The compound of claim 1 wherein $E_1$ is H, a hydroxyl protecting group, or an activated solid support.

6. The compound of claim 1 wherein $E_2$ is trityl, methoxytrityl, dimethoxytrityl or trimethoxytrityl.

7. The compound of claim 1 wherein $E_2$ is H or a hydroxyl protecting group.

8. The compound of claim 1 wherein $Z_2$ is H.

9. The compound of claim 1 wherein $Z_1$ is a purine or a pyrimidine.

10. The compound of claim 9 wherein $Z_1$ is adenine, guanine, cytosine, uridine or thymine.

11. The compound of claim 1 wherein $Z_1$ is alkyl having 1 to about 20 carbon atoms.

12. The compound of claim 1 wherein $Z_1$ is aryl having 6 to about 14 carbon atoms or aralkyl having 7 to about 15 carbon atoms.

13. The compound of claim 1 wherein $Z_1$ is fluorenylmethyl, phenyl, or benzyl.

14. The compound of claim 1 wherein $Z_1$ is polyethylene glycol or glutamyl.

15. The compound of claim 1 wherein m is from about 1 to about 25.

16. The compound of claim 1 wherein X is O.

17. The compound of claim 1 wherein X is S.

18. The compound of claim 1 wherein said

groups are of a predetermined sequence.

19. The compound of claim 1 wherein said

groups are of a random sequence.

20. The compound of claim 1 wherein at least one of said $L_0$, $L_m$, and $L_{m+1}$ groups is different from other of said $L_0$, $L_m$, and $L_{m+1}$ groups.

21. A chimeric oligomeric compound having a first region comprising a phosphodiester or phosphorothioate oligonucleotide and a second region having the structure:

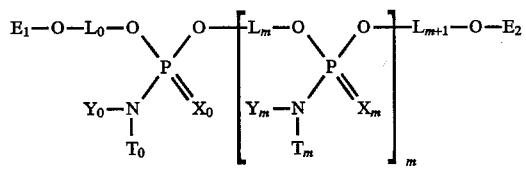

wherein: $X_0$ and each $X_m$, independently, are O or S;

$Q_1$, $Q_2$, $L_0$, $L_{m+1}$ and each $L_m$, independently, are $C_2$-$C_{10}$ alkyl, $C_2$-$C_{10}$ alkenyl, $C_2$-$C_{10}$ alkynyl, $C_4$-$C_7$ carbocylo alkyl or alkenyl, a heterocycle, an ether having 2 to 10 carbon atoms and 1 to 4 oxygen or sulfur atoms, a polyalkyl glycol, or $C_7$-$C_{14}$ aralkyl;

$Y_0$ and each $Y_m$, independently, are H, or $[Q_2]_j$—$Z_2$;

$T_0$ and each $T_m$, independently, are $[Q_1]_k$—$Z_1$, or together Y and T are joined in a nitrogen heterocycle;

j and k independently are 0 or 1;

m is 1 to about 50;

$Z_1$ and $Z_2$, independently, are H, $C_1$-$C_2$ alkyl, $C_2$-$C_{20}$ alkenyl, $C_2$-$C_{20}$ alkynyl, $C_6$-$C_{14}$ aryl, $C_7$-$C_{15}$ aralkyl, a halogen, CH=O, $OR_1$, $SR_2$, $NR_3R_4$, C(=NH)$NR_3R_4$, CH($NR_3R_4$), NHC(=NH)$NR_3R_4$, CH($NH_2$)C(=O)OH, C(=O)$NR_3R_4$, C(=O)$OR_5$, a metal coordination group, a reporter group, a nitrogen-containing heterocycle, a purine, a pyrimidine, a phosphate group, a polyether group, or a polyethylene glycol group;

$R_1$ is H, alkyl having 1 to about 6 carbon atoms, or a hydroxyl protecting group;

$R_2$ is H, alkyl having 1 to about 6 carbon atoms, or a thiol protecting group;

$R_3$ and $R_4$ are, independently, H, alkyl having 1 to about 6 carbon atoms, or an amine protecting group;

$R_5$ is H, alkyl having 1 to about 6 carbon atoms, or an acid protecting group; and where one of $E_1$ and $E_2$ comprises said phosphodiester or phosphorothioate oligonucleotide and the other of said $E_1$ and $E_2$ is H, a hydroxyl protecting group or a conjugate group.

* * * * *

UNITED STATES PATENT AND TRADEMARK OFFICE
CERTIFICATE OF CORRECTION

PATENT NO. : 5,637,684
DATED : June 10, 1997
INVENTOR(S) : Phillip D. Cook, Oscar Acevedo, Normand Hebert It is certified that error appears in the above-indentified patent and that said Letters Patent is hereby corrected as shown below:

Column 10, line 50, please delete "in-flammatory" and substitute -- inflammatory -- therefor;

Column 14, line 37, please delete "08/1179," and substitute -- 08/179 -- therefor;

Column 14, line 64, please delete "08/1179,970" and substitute -- 08/179,970 -- therefor;

Column 18, line 24, please delete "‾P" and substitute -- $^{31}$P -- therefor;

Column 18, line 56, please delete "(0.029" and substitute -- (.029 -- therefor;

Column 20, line 8, please delete "‾P" and substitute -- $^{31}$P -- therefor;

UNITED STATES PATENT AND TRADEMARK OFFICE
CERTIFICATE OF CORRECTION

PATENT NO. : 5,637,684
DATED : June 10, 1997
INVENTOR(S) : Phillip D. Cook, et. al.

It is certified that error appears in the above-identified patent and that said Letters Patent is hereby corrected as shown below:

Column 27, line 2, please delete "$_2$M" and substitute --2M-- therefor.

Signed and Sealed this

Twentieth Day of October, 1998

Attest:

BRUCE LEHMAN

Attesting Officer   Commissioner of Patents and Trademarks